(12) United States Patent
Lowell et al.

(10) Patent No.: US 9,733,198 B2
(45) Date of Patent: Aug. 15, 2017

(54) METHOD AND APPARATUS FOR IMPROVED SAMPLING RESOLUTION IN X-RAY IMAGING SYSTEMS

(71) Applicant: NOVARAY MEDICAL, INC., Newark, CA (US)

(72) Inventors: Augustus Percival Lowell, Durham, NH (US); Tobias Funk, Martinez, CA (US); Chwen-Yuan Ku, San Jose, CA (US); Josh Star-Lack, Palo Alto, CA (US); Edward Gerald Solomon, Melno Park, CA (US); Winston Y. Sun, Palo Alto, CA (US)

(73) Assignee: NOVARAY MEDICAL, INC., Newark, CA (US)

(*) Notice: Subject to any disclaimer, the term of this patent is extended or adjusted under 35 U.S.C. 154(b) by 0 days.

(21) Appl. No.: 14/977,279

(22) Filed: Dec. 21, 2015

(65) Prior Publication Data

US 2016/0123902 A1  May 5, 2016

Related U.S. Application Data

(63) Continuation of application No. 13/738,614, filed on Jan. 10, 2013, now Pat. No. 9,217,719.

(51) Int. Cl.
| | |
|---|---|
| G21K 5/04 | (2006.01) |
| G01N 23/04 | (2006.01) |
| A61B 6/00 | (2006.01) |
| H01J 35/04 | (2006.01) |
| H01J 35/06 | (2006.01) |
| A61B 6/02 | (2006.01) |

(52) U.S. Cl.
CPC ............... *G01N 23/04* (2013.01); *A61B 6/40* (2013.01); *A61B 6/4233* (2013.01); *A61B 6/5205* (2013.01); *H01J 35/04* (2013.01); *H01J 35/065* (2013.01); *A61B 6/025* (2013.01); *A61B 6/4007* (2013.01); *A61B 6/487* (2013.01)

(58) Field of Classification Search
CPC ........ G01N 23/04; A61B 6/40; A61B 6/4233; A61B 6/5205; A61B 6/025; A61B 6/4007; A61B 6/487; H01J 35/04; H01J 35/065
USPC .... 378/62, 91, 119, 124, 125, 134, 135, 143
See application file for complete search history.

(56) References Cited

U.S. PATENT DOCUMENTS

| | | |
|---|---|---|
| 5,550,378 A | 8/1996 | Skillicorn et al. |
| 5,610,967 A | 3/1997 | Moorman et al. |
| 5,644,612 A | 7/1997 | Moorman et al. |
| 5,651,047 A | 7/1997 | Moorman et al. |

(Continued)

FOREIGN PATENT DOCUMENTS

EP          1211917          6/2002

*Primary Examiner* — Nicole Ippolito

(57) ABSTRACT

The present invention pertains to an apparatus and method for X-ray imaging wherein a radiation source comprising rows of discrete emissive locations can be positioned such that these rows are angularly offset relative to rows of sensing elements on a radiation sensor. A processor can process and allocate responses of the sensing elements in appropriate memory locations given the angular offset between source and sensor. This manner of allocation can include allocating the responses into data rows associated with unique positions along a direction of columns of discrete emissive locations on the source. Mapping coefficients can be determined that map allocated responses into an image plane.

19 Claims, 12 Drawing Sheets

(56) References Cited

U.S. PATENT DOCUMENTS

| | | |
|---|---|---|
| 5,682,412 A | 10/1997 | Skillicorn et al. |
| 5,729,584 A | 3/1998 | Moorman et al. |
| 5,751,785 A | 5/1998 | Moorman et al. |
| 5,808,306 A | 9/1998 | Skillicorn et al. |
| 5,835,561 A | 11/1998 | Moorman et al. |
| 5,859,893 A | 1/1999 | Moorman et al. |
| 6,060,713 A | 5/2000 | Skillicorn et al. |
| 6,118,853 A | 9/2000 | Hansen et al. |
| 6,118,854 A | 9/2000 | Solomon et al. |
| 6,157,703 A | 12/2000 | Solomon et al. |
| 6,175,611 B1 | 1/2001 | Melen et al. |
| 6,178,223 B1 | 1/2001 | Solomon et al. |
| 6,181,764 B1 | 1/2001 | Solomon et al. |
| 6,183,139 B1 | 2/2001 | Solomon et al. |
| 6,198,802 B1 | 3/2001 | Elliott et al. |
| 6,208,709 B1 | 3/2001 | Melen |
| 6,234,671 B1 | 5/2001 | Solomon et al. |
| 6,649,914 B1 | 11/2003 | Moorman et al. |
| 7,062,006 B1 | 6/2006 | Pele et al. |
| 9,217,719 B2 * | 12/2015 | Lowell .................... H01J 35/04 |
| 2006/0045234 A1 | 3/2006 | Pelc et al. |
| 2008/0025461 A1 * | 1/2008 | Foland ................. G01N 23/046 378/17 |
| 2008/0175350 A1 * | 7/2008 | MacDonald ........... G01N 23/20 378/37 |
| 2011/0135051 A1 | 6/2011 | Fadler et al. |

\* cited by examiner

METHOD AND APPARATUS FOR IMPROVED SAMPLING RESOLUTION IN X-RAY IMAGING SYSTEMS

CROSS REFERENCE TO RELATED APPLICATION

This application is a Continuation Application of the commonly-owned U.S. patent application Ser. No. 13/738,614, U.S. Pat. No. 9,217,719, filed Jan. 10, 2013, by A. Lowell et al., and entitled "Method and Apparatus for Improved Sampling Resolution in X-Ray Imaging Systems," which is hereby incorporated by reference in its entirety.

FIELD OF THE INVENTION

The present invention pertains to X-ray imaging systems. The present invention pertains more specifically to X-ray imaging systems utilizing sources having a plurality of discrete emissive locations.

BACKGROUND

Point-source X-ray imaging systems currently account for the greatest portion of medical X-ray imaging systems in the United States. Point-source X-ray imaging systems comprise an X-ray radiation source such as an X-ray tube that emits X-rays from a single discrete location or window. While point-systems have achieved a relatively high level of image resolution and imaging speed, they are limited by an unfavorable signal-to-noise ratio related to the position of the patient relative to the source and detector and provide data sufficient only for flat, e.g. two-dimensional, images.

X-ray imaging systems have been developed that address these latter two deficiencies. See for example U.S. Pat. No. 5,729,584 entitled "Scanning Beam X-Ray Imaging System," issued to Moorman et al. In contrast to a point-source imaging system, this type of imaging systems utilizes an X-ray source having a plurality of discrete emissive locations on its face and a relatively small detector. The geometry of this type of imaging system both improves signal-to-noise ratios by decreasing the number of scattered X-ray photons collected and provides sufficient data to reconstruct a range of planes between the source and detector.

However, the spatial resolution and image fidelity provided by these systems can vary from plane to plane, and can range from being competitive with or better than advanced point-source systems and being quite poor. Embodiments of the present invention provide a method and apparatus of improving the resolution and image fidelity of such systems.

SUMMARY

The present invention pertains to an apparatus and method for X-ray imaging wherein a radiation source comprising rows of discrete emissive locations can be positioned such that these rows are angularly offset relative to rows of sensing elements on a radiation sensor. The angular offset can be less than 90 degrees or less than 5 degrees, or may displace a sensing element by a length equal to an integer number of sensing elements, including one, two, or three sensing elements. A processor can process and allocate responses of the sensing elements into appropriate memory locations given the angular offset between source and sensor. This manner of allocation can include allocating the responses into data rows associated with unique positions along the direction of columns of discrete emissive locations on the source. Mapping coefficients can be determined that map allocated responses into an image plane. Responses can be mapped along a first dimension, aggregated, and then mapped along the second dimension, or may be mapped directly into an image plane.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

U.S. Pat. No. 5,729,584 entitled "Scanning Beam X-Ray Imaging System," U.S. Pat. No. 6,876,724 entitled "Large-Area Individually Addressable Multi-Beam X-Ray System and Method of Forming the Same," both of which are hereby incorporated by reference, describe X-ray imaging systems utilizing sources that emit radiation from a plurality of discrete locations on their faces and spatially resolved sensors. These and similar imaging systems can acquire sufficient data to reconstruct multiple image planes between the source and sensor and can be useful for fluoroscopic guidance, image acquisition for computed tomography, and other applications.

Examples of a source capable of emitting radiation from a plurality of discrete locations may be an array of carbon nanotube cathodes or other nanotube cathodes, scanning electron beam sources, scanning laser sources, and arrays of single cathode emitters.

Spatially resolved sensors in imaging systems of the present invention may comprise a sensor array of small sensors or sensor elements, e.g. a pixelated detector. A sensor array may comprise elements or pixels of photon-counting detectors, energy-integrating detectors, energy-resolving detectors, or any type of detector sensitive to X-ray photons. A single sensor element or pixel may not be spatially resolved, e.g. the location within an individual sensor element where a photon strikes may not be recoverable, but a sensor array can be spatially resolved by associating data with the position of the sensor element or pixel from which it is received.

Figure 1:
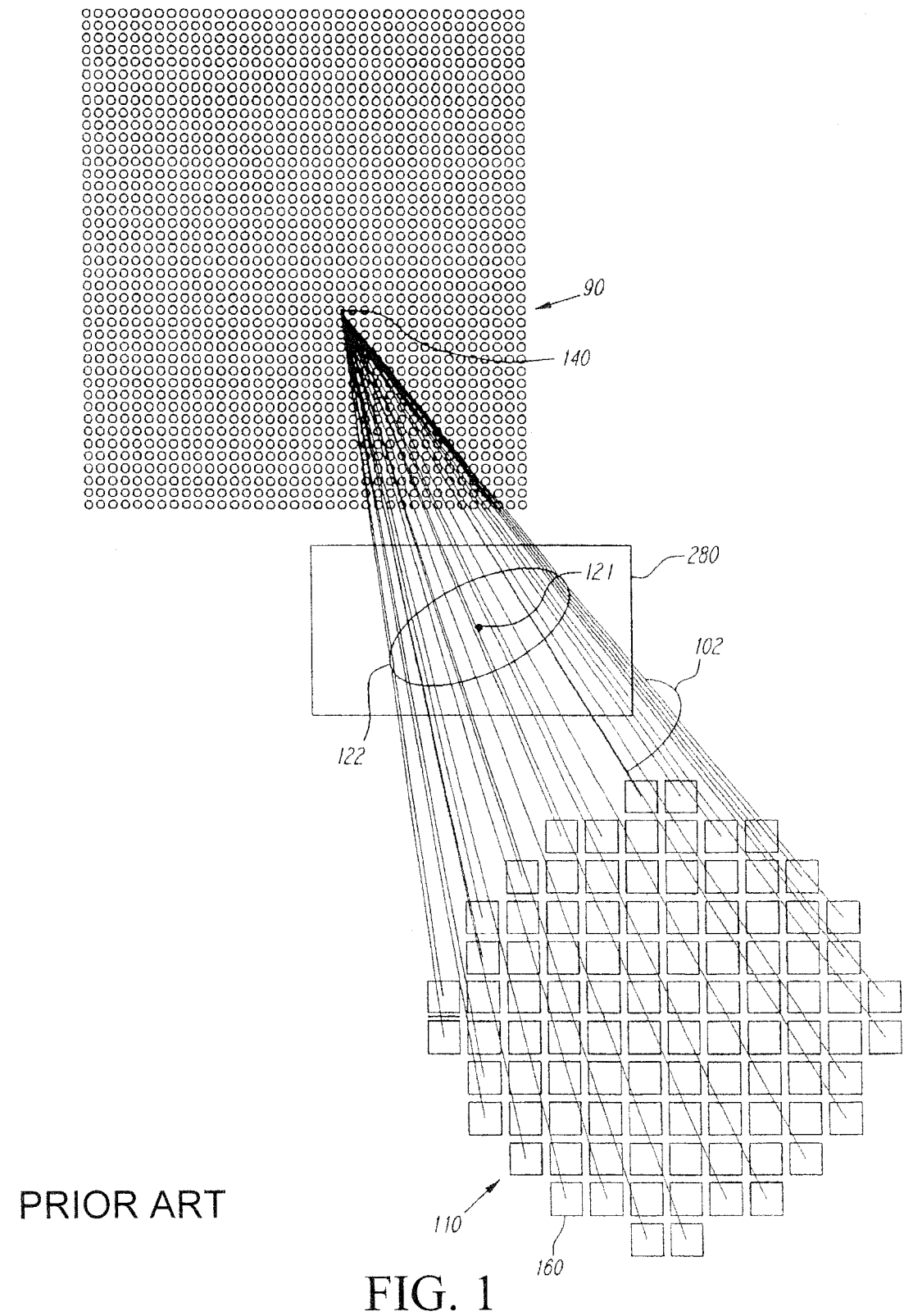
FIG. 1 is a diagram which illustrates the illumination of a region or patch of an image plane by a discrete source location.

FIG. 1 is a diagram which illustrates the illumination of a region or patch of an image plane by a discrete source location. The diagram of FIG. 1 illustrates how discrete source location 140 of source 90 can illuminate patch 122 in image plane 280 by emitting rays 102. After passing through an imaging volume, rays 102 are incident on sensor 110. A data set containing the response of elements of sensor 110 corresponding to emission by discrete source location 140 may be processed or stored in a memory buffer or buffers to be used in conjunction with sensor data corresponding to emissions by other discrete source locations for reconstruction of image plane 280.

Figure 2:
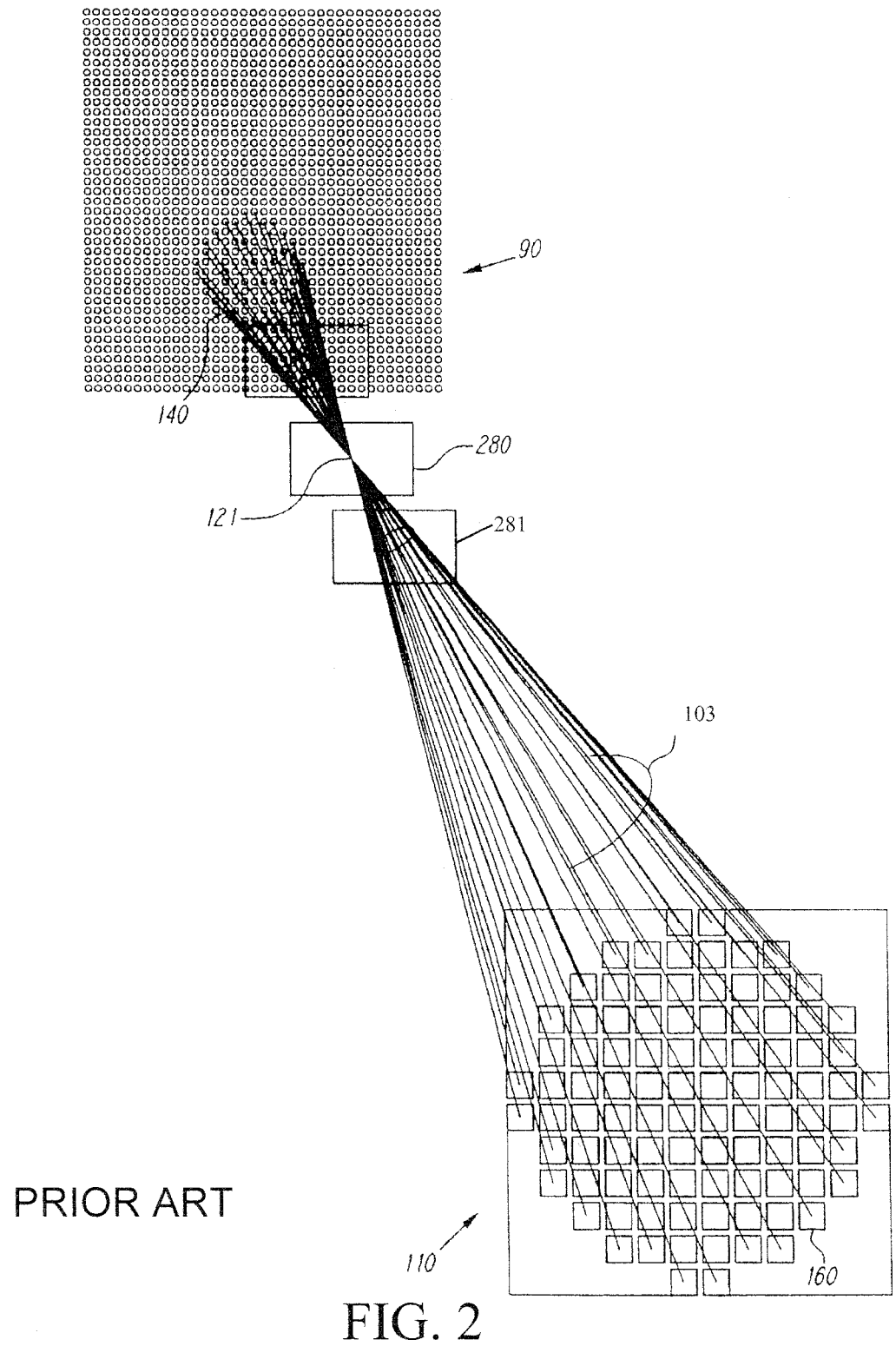
FIG. 2 is a diagram which illustrates the sampling of a single point in an image plane by multiple discrete source locations.

FIG. 2 is a diagram which illustrates the sampling of a point in an image plane by multiple discrete source locations and sensor elements, demonstrating how a single point in an image plane may be sampled by multiple discrete source locations. Plurality of rays 103, all of which sample point 121, may not be emitted simultaneously but at unique points in time, e.g. upon the firing of each discrete source location. Data from sensor array 110 corresponding to multiple source locations can be summed and normalized, averaged, or otherwise combined to determine probable X-ray attenuation properties of point 121. Other points in image plane 280 can be assigned relative intensity values similarly.

The subsets of discrete source locations and sensor elements which sample a given point in an image plane, e.g. the discrete source locations that emit and sensor elements that receive plurality of rays 103 to sample point 121 in image plane 280, are related to the position of said image plane between the source and sensor array. While plurality of rays 103 can be grouped together to reconstruct point 121 in image plane 280, plurality of rays 103 samples a plurality of different points in subsequent image plane 281. Multiple image planes within the space between a source and sensor can be imaged by processing and combining data according to ray intersections with the respective planes. An individual plane can be selected for viewing, or multiple planes can be combined to provide three-dimensional depth.

A plurality of rays may or may not converge to a point or points in subsequent image plane 281 as rays 103 converged to point 121 in image plane 280. The convergence seen in plane 280 can actually have negative effects for resultant image quality, since rays 103 all sample a single point, providing essentially redundant information, rather than a plurality of points in the image plane which could all contribute meaningful information for the population of image plane with accurate pixel values. The manner in which rays connecting discrete source locations to detector elements converge or fail to converge in various image planes can determine the sampling resolution of the system and thereby the accuracy, spatial resolution or quality of resultant images.

Sampling resolution may be characterized as the average number of points sampled per image pixel. Image pixels can be defined by dividing an image plane into a grid of predetermined dimensions, and taking each square or rectangle of the grid to be an image pixel. Characterizing the average number of sample points, e.g. ray intersections, per image pixel rather than total points per image plane may be preferable, as points may not necessarily be distributed evenly within a plane. Having a high sampling resolution, e.g. a number of sampled points within most or all pixels, can be important for a number of reasons. At a minimum, having a sampling resolution of at least one point per pixel is necessary to assign a measured value to each pixel in an image. Greater sampling resolution can however be necessary to avoid aliasing or other distortions and inaccuracies.

An imaging volume may contain features that are smaller or finer than a single image pixel; regions within an image pixel may provide varying amounts of X-ray attenuation. If an image pixel is sampled at only one or a few points, the value which will be assigned to that pixel may reflect the properties of the single feature or few features within the pixel that are sampled, which may or may not be a good representation of the pixel as a whole. If an image pixel is instead sampled at a large number of points, the pixel can be assigned a value based on the average properties measured throughout the pixel and likely be a more accurate representation. For example, if an image pixel is mostly X-ray transparent but has a relatively small, X-ray opaque feature, the reconstructed pixel may be assigned a very bright value if it happens to be sampled only at the small opaque feature. However, if said pixel were sampled at a number of points throughout its area, it may instead be assigned a dim value, representing the average of a small number of sample points falling on the opaque features and a large number of sample points falling on the X-ray transparent regions.

Other types of aliasing or prealiasing can occur when sampling resolution is low, particularly when an image has repeating, e.g. sinusoidal, features. The Nyquist criterion for signal processing shows that the frequency at which a signal is sampled must be at least twice the frequency of the highest frequency signal component to avoid aliasing, e.g. a type of distortion wherein a high-frequency component is reconstructed as a relatively lower frequency component. Analogously for image processing, a sampling resolution at least twice as narrow as the width of the finest features in an image plane may be desirable to avoid aliasing.

Sampling resolution can affect the spatial resolution and fidelity of reconstructed images. In existing tomosynthetic imaging systems some image planes tend to have poor sampling resolution due to the convergence of rays at a small number of sample points.

Figure 3:
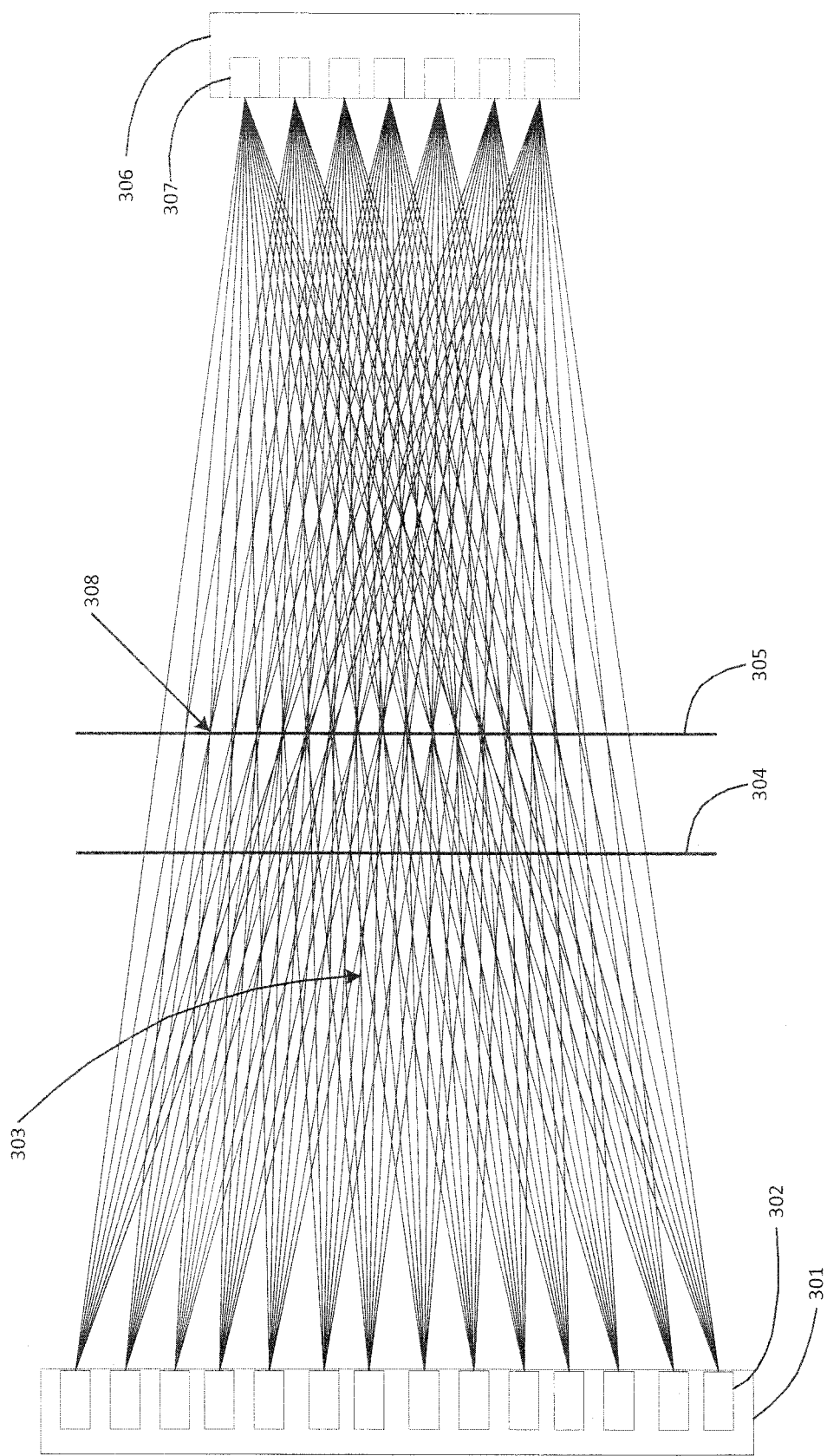
FIG. 3 is a diagram representing a two-dimensional cross-section of subsets of a source comprising an array of discrete source locations and a sensor comprising an array of sensor elements.

FIG. 3 is a diagram representing a two-dimensional cross-section of subsets of a source comprising an array of discrete source locations and a sensor comprising an array of sensor elements. Source subset 301 represents a row of discrete sources such as discrete source 302, and sensor subset 306 represents a row of sensor elements such as sensor element 307. Rays 303 are emitted by discrete sources and detected by sensor elements 307. There exist planes, e.g. lines in this two-dimensional cross-section, between source subset 301 and sensor subset 306 where little if any convergence exists among rays 303. For example, in evenly sampled image plane 304 rays 303 sample a large number of well-spaced points in the image plane. However, there also exist planes where rays 303 converge and sample relatively few points. For example, in sparsely sampled plane 305 rays 303 converge at points such as convergent point 308, reducing the sampling resolution of the plane. It can be inferred that similar patterns can arise along both dimensions of a source array and sensor and that there can be significant variations in sampling resolution between planes in the imaging volume of a tomosynthetic imaging system.

Figure 4:
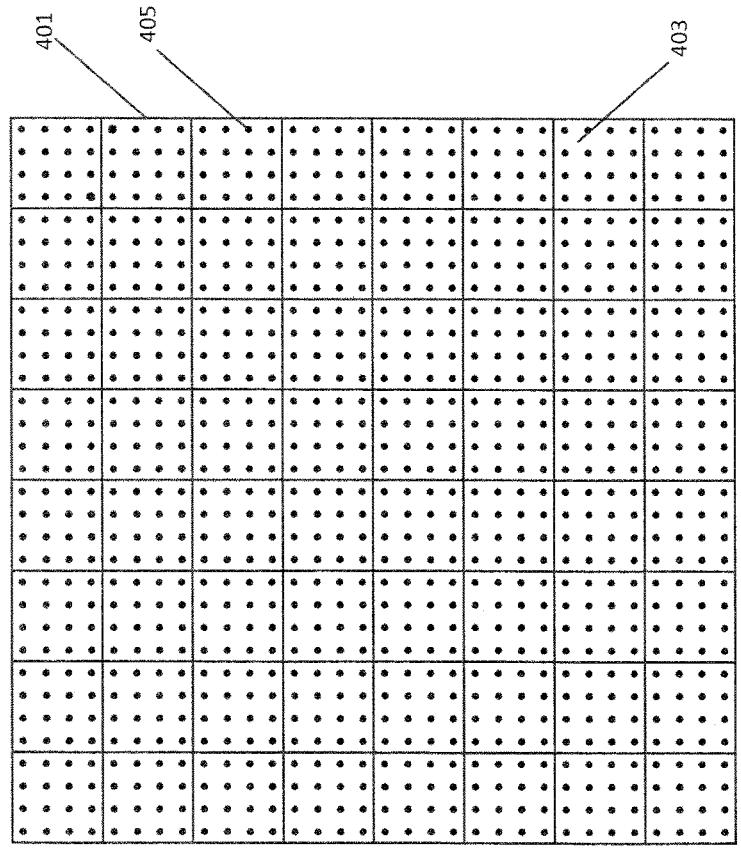
FIG. 4 is a diagram representing a possible sampling pattern in an array of image pixels within a relatively evenly or well-sampled image plane.

FIG. 4 is a diagram representing a possible sampling pattern in an array of image pixels within a relatively evenly or well-sampled image plane. The sampling patterns of pixel array 401 comprises sample points such as sample point 405, which represent points at which rays traveling from a discrete source location to sensor elements intersect said image plane. It can be seen that in pixel array 401 sixteen intersection points occur within every pixel. This is equivalent to saying that the sampling resolution in pixel array 401 will be approximately 16 points per pixel, or alternatively quoted per dimension as ¼ of a pixel. The value assigned to each pixel, e.g. pixel 403, upon image reconstruction may be a weighted sum, average, or other combination of sixteen sample points.

Figure 5:
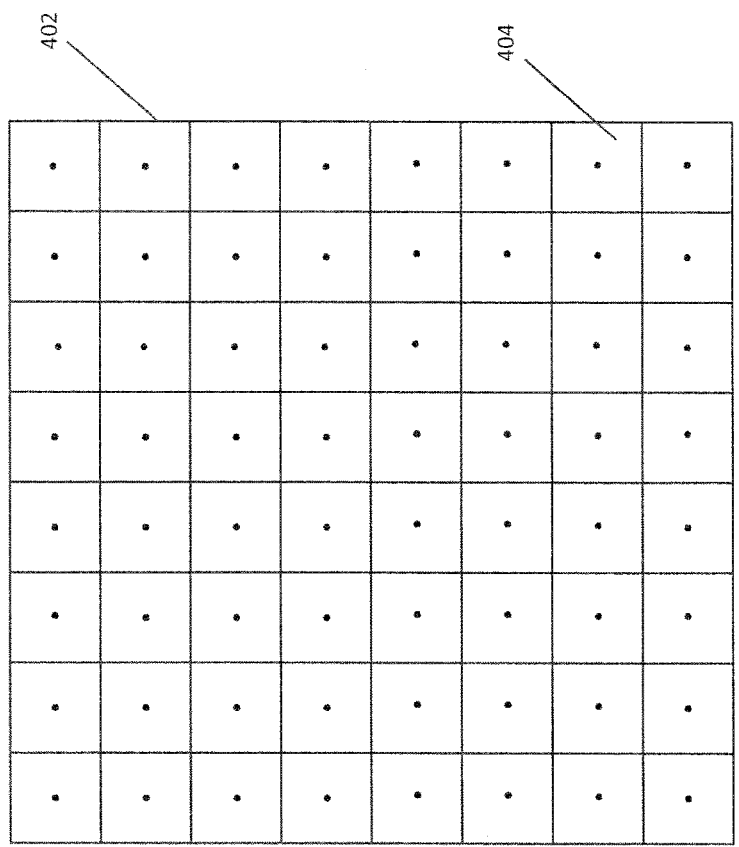
FIG. 5 is a diagram representing a possible sampling pattern in an array of image pixels within an image plane wherein rays converge significantly.

Sampling patterns may be simulated by calculating the center of every sensors in a given array, back-projecting rays from each sensor to an array of discrete source locations, and recording ray intersection points in a grid of imaging pixels for a selected imaging plane. FIG. 5 is a diagram representing a possible sampling pattern in an array of image pixels within an image plane wherein rays converge significantly.

In contrast to the relatively populated sampling pattern and quarter-pixel resolution seen in pixel array 401 of FIG. 4, pixel array 402 exhibits a sampling resolution of only one pixel. As pixel array 401 and pixel array 402 represent image planes or subsets of image planes located at different distances between the same source and sensor, it may be inferred that each sample point within pixel array 402 is sampled by more than one, e.g. sixteen, rays.

The presence and locations of ray convergence points can be related to the geometry of a tomosynthetic imaging system, namely, to the relative positions of discrete source locations and sensor elements. Since the sampling pattern in an image plane is created by the intersection of rays connecting discrete source locations with sensor elements, changing position parameters of source locations or sensor elements can change the sampling patterns of each image plane. Referencing FIG. 3 for example, changing the spacing between discrete sources in source subset 301 may change the distances from source subset 301 at which evenly sampled plane 304 or sparsely sampled plane 305 are located. Changing the spacing between sensor elements in sensor subset 306 may also affect the locations of evenly or well-sampled and sparsely sampled planes.

Embodiments of the present invention provide manners of improving the sampling resolution of tomosynthetic imaging systems.

Figure 6:
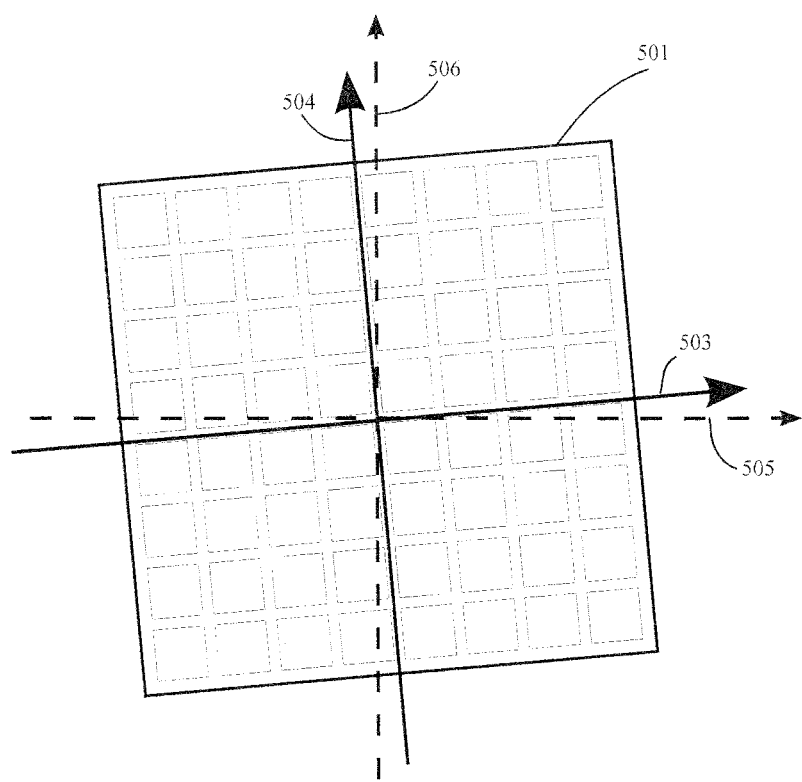
FIG. 6 is a diagram showing a sensor that is positioned angularly offset with respect to a source, the source's alignment being represented by a pair of x- and y-axes.

In one embodiment of the present invention, a sensor array is angularly offset such that x- and y-axes of the sensor, defined for the present embodiment as axes to which rows and columns, respectively, of sensor elements run parallel, are not angularly aligned with the x- and y-axes of a source, to which rows and columns, respectively, of discrete source locations run parallel. FIG. 6 is a diagram showing a sensor that is positioned angularly offset with respect to a source, the source's alignment being represented by a pair of x- and y-axes. X-axis 505 and y-axis 506 represent the directions of rows and columns of discrete emissive locations on a source face, respectively. Offset x-axis 503 and offset y-axis 504 align with rows and columns of sensor face 501. In this embodiment of the present invention, the axes of sensor face 501 are not angularly aligned with x-axis 505 and y-axis 506; rows and columns of the sensor are not angularly aligned with rows and columns of the source.

Figure 8:
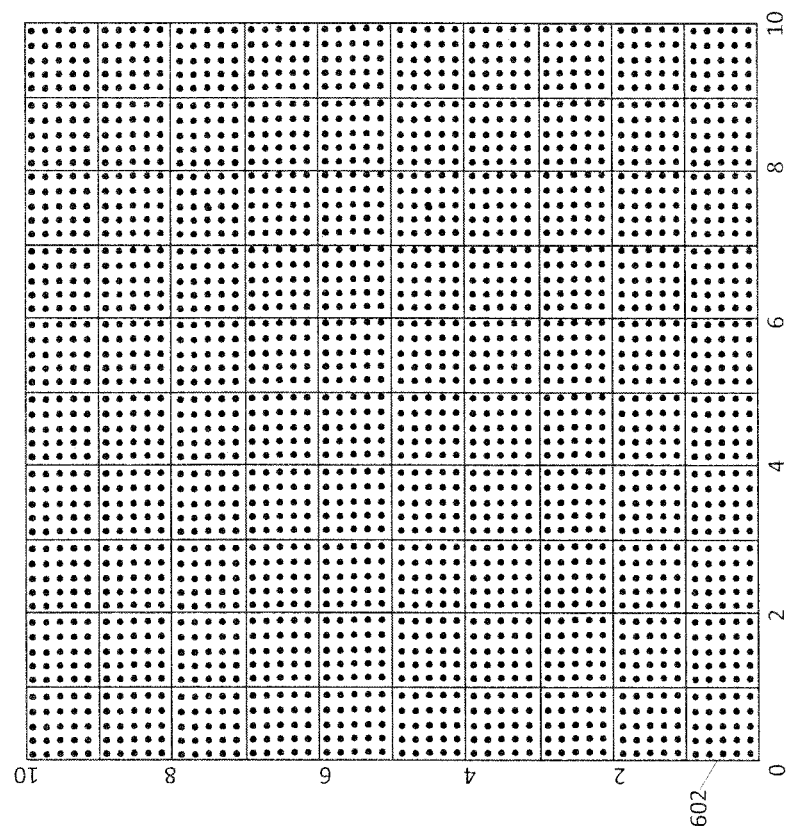
FIG. 8 is a diagram representing an image plane wherein the sampling pattern is generated by an angularly offset source and sensor of an embodiment of the present invention.
Figure 7:
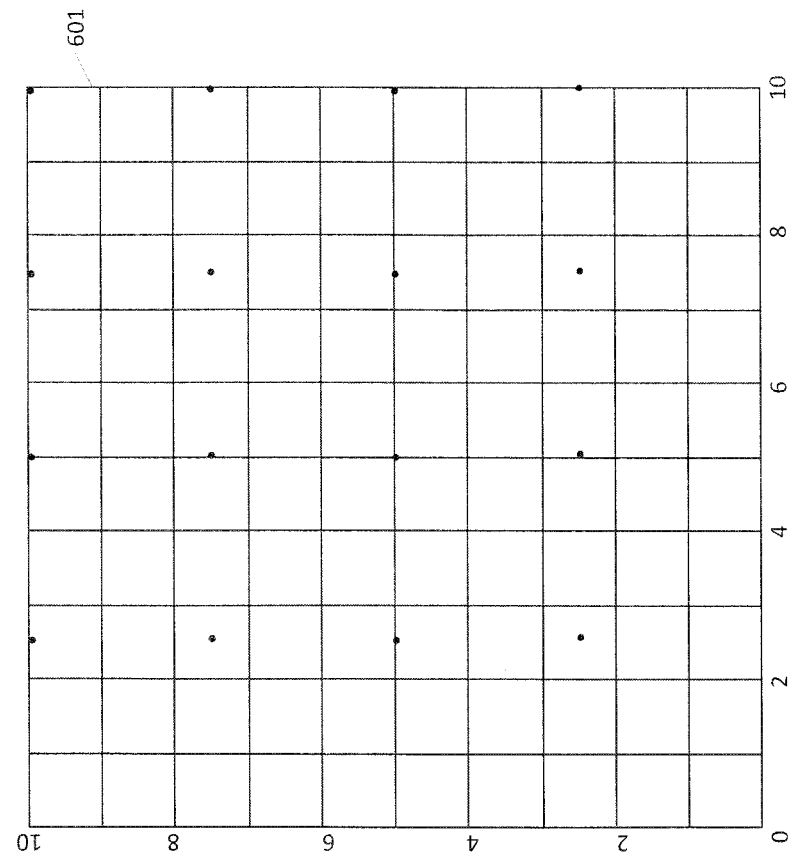
FIG. 7 is a diagram representing the sampling pattern of an image plane that would be generated by an aligned source and sensor, which has worse than 1 pixel sampling resolution.

An effect of having an angular offset between the source and sensor in this embodiment may be to separate rays which would otherwise converge, e.g. that would sample the same point if the source and sensor were aligned. FIG. 7 is a diagram representing the sampling pattern of an image plane that would be generated by an aligned source and sensor, which has worse than 1 pixel sampling resolution. FIG. 8 is a diagram representing the same image plane as FIG. 7, but where the sampling pattern is generated by an angularly offset source and sensor of an embodiment of the present invention. In the embodiment of FIG. 8 an even, well-populated sampling of the image plane is achieved; sampling resolution is approximately ⅕ of a pixel, a significant increase from the sampling resolution of this plane generated by an aligned source and sensor as shown in FIG. 7.

Angularly offsetting a sensor array can alleviate sampling redundancy not only in very sparsely sampled planes but also in image planes where any amount of ray convergence exists; offsetting a sensor by a predetermined amount does not merely shift points of convergence among different image planes in the same way that changing the spacing of source locations or sensor elements may but can improve sampling resolution throughout the imaging space of a system.

Figure 9:
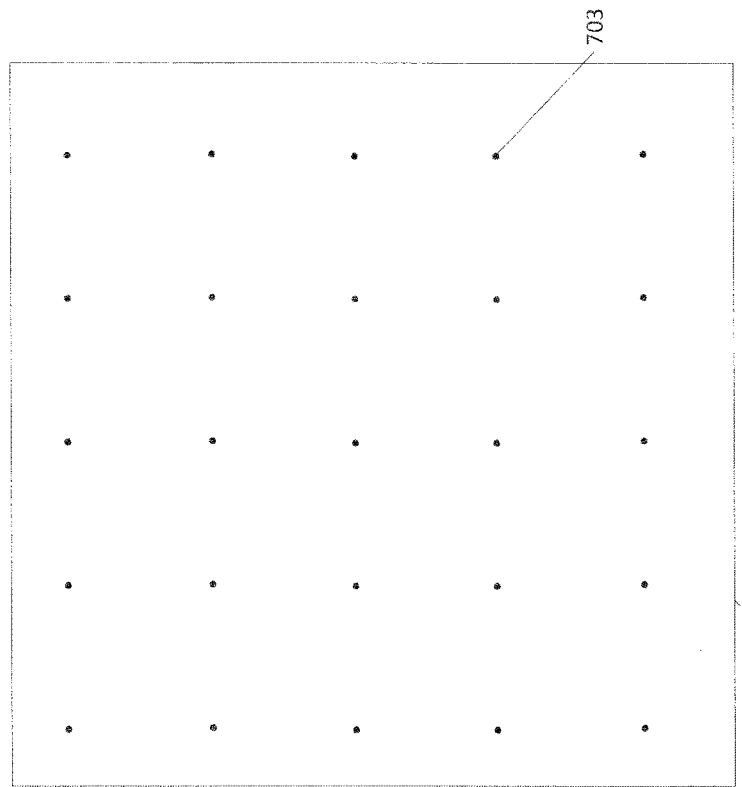
FIG. 9 is a diagram showing the simulated sampling pattern of a single pixel within an evenly sampled image plane between an angularly aligned source and sensor.

FIG. 9 is a diagram showing the simulated sampling pattern of a single pixel within an evenly sampled image plane between an angularly aligned source and sensor. Additional parameters of the simulation included a distance between source and sensor arrays being 1.5 meters and the spacing of sensors in the sensor array, e.g. center-to-center distances, being 0.114 cm. If the pixel of FIG. 9 is representative of other pixels in its image plane, the sampling resolution of the plane may be approximately ⅕ of a pixel.

Figure 10:
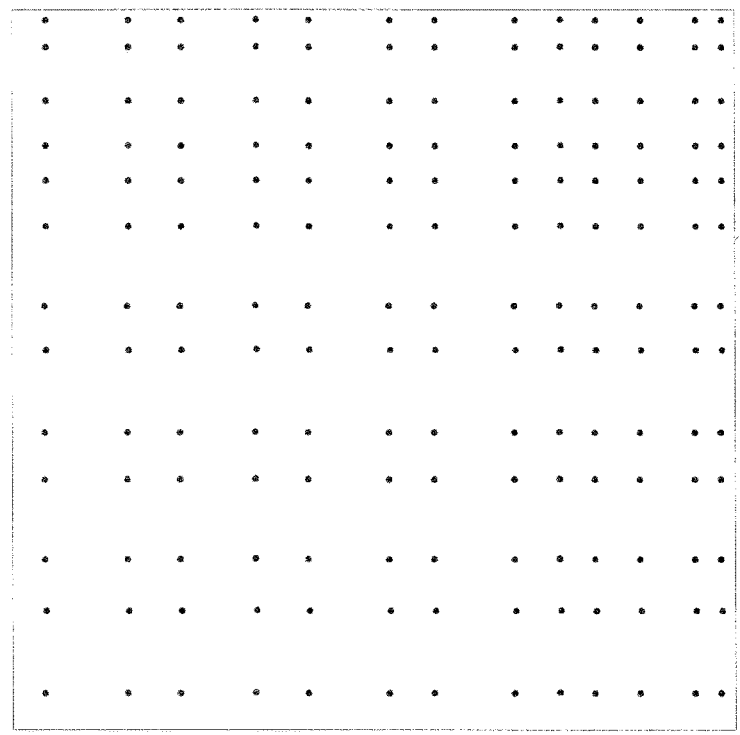
FIG. 10 is a diagram showing the simulated sampling pattern of a single pixel with the sensor being offset relative to the source by 3 degrees in one embodiment of the present invention.

FIG. 10 is a diagram showing the simulated sampling pattern of the same single pixel as FIG. 9 but with the sensor being offset relative to the source by 3 degrees. The increased number of sampling points in the pattern of FIG. 10 suggests that some amount of sampling redundancy, e.g. ray convergence, may have been present in the sampling pattern shown in FIG. 9 despite the pixel being relatively well sampled. Simulations can show that in one embodiment of the present invention, a 3 degree sensor offset may improve imaging resolution to approximately ⅑ of a pixel, or by 80% relative to a non-rotated configuration, in a given plane between source and sensor. It can also be shown for the same parameters that other planes between source and sensor also have improved sampling resolutions.

Angular offsets between a source and sensor array in embodiments of the present invention are not limited to 3 degrees or any other number of degrees. An offset may be any number of degrees between 0 and 360 degrees. Angular offsets in embodiments of the present invention may further be between 0 and 90 degrees, 0 and 45 degrees, 0 and 30 degrees, 0 and 20 degrees, 0 and 10 degrees, or 0 and 5 degrees, inclusive. For example, an angular offset may be 1, 2, 3, 4, 5, 6, 7, 8, 9, 10, 11, 12, 13, 14, or 15 degrees. Angular offsets need not be integer number of degrees and may be rational or irrational fractions of degrees, such as less than 1 degree, between 1 and 2 degrees, between 2 and 3 degrees, between 3 and 4 degrees, between 4 and 5 degrees, or any other fractional number of degrees. For example, an angular offset may be any number of degrees, including zero, plus or minus ⅛, 1/7, ⅙, ⅕, ¼, ⅓, ½ a degree, or other fractional or decimal numbers of degrees.

However, there may be angular offsets that do not yield spatial resolution benefits, particularly if the sensor has some amount of rotational symmetry. For example, for a square sensor array, or any other sensor array with 4-fold rotational symmetry, an angular offset of ninety degrees or any multiple of ninety degrees may recreate the same sampling scenario as a non-offset sensor. For a rectangular sensor array, or any other sensor array with 2-fold rotational symmetry, an angular offset of 180 degrees or any multiple of 180 degrees may recreate the same sampling scenario as a non-offset sensor array. Rotating a sensor array by an angle which is rotationally symmetric to a non-angularly offset sensor array, e.g. rotating a sensor array of n-fold rotational symmetry by an angle of 360/n degrees, may not result in spatial resolution benefits.

Amounts of angular offset in embodiments of the present invention may also be characterized as a number of "elements per full length" of the sensor. "Elements per full length" may refer to the fractional or whole number of sensor elements or pixels by which a corner of the sensor is displaced, e.g. vertically or horizontally, from its non-offset position. For example, a counterclockwise sensor angular offset may displace the upper right corner of the sensor array upwards vertically and leftward horizontally. The absolute difference between its initial vertical position and its offset vertical position may be divided by the height of sensor elements to yield a fractional or whole number of sensor elements per full length, or the absolute difference between its initial horizontal position and its offset horizontal position may be divided by the width of a sensor elements to yield a fractional or whole number of sensor elements per full length. This manner of characterization may be particularly useful due to the relationship between sampling patterns and geometries of the source and sensor, specifically, to the size and spacing of discrete emissive locations on a source or elements on a sensor face.

Angular offsets in embodiments of the present invention can be any whole or fractional number of elements per full length, including by less than one element per full length. An optimal degree of sensor angular offset or rotation, e.g. a number of elements per full length that results in the best sampling resolution, may be an integer number of elements per full length of the sensor. For example, in one embodiment of the present invention, a sensor is rotated by one sensor element per full length of the array, and in another embodiment, two elements per full length of the sensor array. Both of these embodiments may exhibit optimized sampling performance. Other integer angular offsets of 3, 4, 5, 6, 7, 8, 9, 10, 11, 12, 14, 15, or any other integer number of elements per full length of the sensor can be utilized. Alternatively, a sensor array may be offset by fractional, non-integer numbers of elements per full length, including but not limited to 1/16, ⅛, ¼, ⅓, ½, ⅔, or ¾ of an individual sensor element, or any other fraction of a sensor element less than, greater than, or between the enumerated values.

Small angles of offset, e.g. small numbers of elements per full length, may utilize available x-ray radiation efficiently; unless an x-ray source or the collimator of an x-ray source is designed for a specific degree of sensor array offset, positioning a sensor array out of alignment with the source may result in some sensor elements being moved out of the paths of X-ray beams into space where no X-rays will be received. For small angular offsets, e.g. 1, 2, or 3 elements per full length, the benefits of improved sampling may be greater than these losses. For relatively large angular offsets, the decrease in elements that will be illuminated by X-ray radiation may become more significant.

In another embodiment of the present invention, a sensor is fabricated with vertical and horizontal offsets between sensor elements along rows and columns, respectively, and utilized for imaging in conjunction with a non-offset source. Vertical and horizontal offsets may be less than the length of one sensor element, and the resultant configuration of sensor elements may be similar to that of a square or rectangular sensor that has been angularly offset by some amount. In an alternative embodiment of the present invention, a source is fabricated with vertical and horizontal offsets between discreet emissive locations along rows and columns, respectively, and utilized for imaging in conjunction with a non-offset sensor. Either of these embodiments of the present invention can improve sampling resolution by creating an angular offset between the directions of rows and columns on a source and sensor.

The benefits of maintaining an angular offset between a source and sensor in embodiments of the present invention may be attributable to the creation of a finer sampling "grid" from an increase in the number of points at which projections of the source array of discrete emissive locations and sensor array of elements or pixels intersect. This effect may be visualized by projecting two square grid patterns, representing the centers of elements of the source and sensor arrays, onto a wall or other surface, and sliding one grid horizontally across the other in increments of approximately one grid square. If the intersection points of the two grids are marked at each increment first for the case where the axes of the two grids are parallel and secondly for the case where the grid being slid has been rotated by a small degree with respect to the stationary grid, a larger number of intersection points between the two grids for the angularly offset case is visible, demonstrating an improvement of vertical resolution. The same process may be repeated sliding one grid vertically to demonstrate an improvement in horizontal resolution.

Existing image reconstruction methods may be insufficient to quickly handle data from a system utilizing an angularly offset sensor and realize the image reconstruction-quality benefits of an offset sensor array. Apart from slightly more complex geometry, back-projection of the views taken from an angularly offset sensor array onto a focal-plane image, e.g. the assignment of sensor data to points in an image plane, may not be much more conceptually difficult than back-projection of views from a non-offset sensor; rays may be traced from sensor elements back to discrete source locations and intersection points in a given image plane determined.

In one embodiment of the present invention, images are reconstructed by geometrical back projections of each sensor datum, e.g. the response or value of each sensor element upon illumination by each discrete source location, into the image plane. In this embodiment, the non-parallel geometry of an imaging system with an angular offset between the source and sensor is accounted for during preliminary steps of a ray back-projection method. In this embodiment, inputs such as the locations of sensor elements on a sensor, e.g. in sensor x-y coordinates, and the angular offset between the source and sensor can be utilized to generate a grid representing offset locations of sensor elements, e.g. in source x-y coordinates.

The generation of a coordinate grid representing offset positions of sensor elements can also be completed using inputs such as predetermined sensor element spacing, e.g. center-to-center distance, sensor dimensions, and the angular offset. Appropriate sensor coordinates can be calculated from given inputs in any one of a number of ways, including but not limited to application of trigonometric relations, such as sine and cosine, to the distance of an element from the geometric center of the sensor array and the angular offset; simulation of the offset sensor array and sampling of sensor locations; or any other method. Rays can be back-projected from the coordinate grid, through image planes to discrete source locations, to determine intersection points with the planes. Monte Carlo or analytical methods may or may not be used to simulate interactions of the rays within the imaging volume and calculate probable attenuation properties of the medium based on sensor data in order to assign pixel values within the image planes.

However, efficient implementations of image plane reconstruction that can support real-time image reconstruction may process rows and columns of sensor array data to be reconstructed independently, in successive pipelined stages. One such implementation is described in U.S. Pat. No. 6,178,223 entitled "Image reconstruction method and apparatus" issued to Solomon et al, herein incorporated by reference in its entirety.

Efficient reconstruction methods may process or map data from a sensor data set along one dimension as it is received but process or map the data along the second dimension following a predetermined amount of data accumulation or aggregation. These methods can reduce the amount of memory required for storing unprocessed data, e.g. by processing in one dimension as the data is received, while also reducing the overall amount of processing that occurs, e.g. by strategically aggregating data for further processing.

A set of sensor data can be generated for the firing of each discrete source location. As illustrated in FIG. 1, a discrete source location can illuminate a portion or "patch" of an image plane to which a corresponding sensor data set can be mapped. Each data set can be processed or mapped along a first dimension, e.g. along its rows, as it is received. For simplicity, rows will be considered to be along a horizontal direction of the image plane and columns along a vertical direction. Row-processing a data set can comprise performing an operation on each sensor datum along a row which maps its horizontal coordinate or index into a horizontal coordinate of the image plane, and therefore into an appropriate image pixel column. When the source and sensor are aligned the operation relating a horizontal coordinates of a sensor datum to a horizontal image plane coordinate may be a scaling factor. Scaling factors may be related to the distance between the source and image plane or between the sensor and image plane and to the horizontal position, e.g. column, of the sensor element.

Hardware, firmware, or software components can be configured to apply appropriate scaling factors, or mapping coefficients, along each row. Sets of mapping coefficients can be calculated in real time based on the position of the plane being reconstructed and passed to row processors or may be stored in the row processors or external memory. One or more of these row processors can be utilized to row process each data set. When the source and sensor are aligned, the same set of mapping coefficients may be applied to every row of a given sensor data set as every row in the data set corresponds to the same set of horizontal coordinates along the sensor.

After row processing, data may be stored in the form of "pseudo-rows," rows associated with sensor element rows but populated with data that has been mapped into the image plane and thereby allocated into image pixel columns. The number of image pixel columns in a pseudo-row may be fewer than the number of columns in the original sensor data set. Pseudo-rows may later be column-processed to complete mapping of the data into a final image. A pseudo-row or number of pseudo-rows from a given data set may be combined or grouped with pseudo-rows from other data sets prior to column processing. Column processing can comprise similar operations as row-processing, where column processors can map vertical sensor coordinates associated with each pseudo-row into coordinates of the image plane and allocate the pseudo-rows into image pixel rows.

This type of method may be termed "separable reconstruction" because the mapping of rows and columns of sensor data into respective rows and columns of image pixels are separable processes. Namely, a sensor data set can be row-processed, e.g. mapped pseudo-rows comprising image pixel-indexed columns, by applying the same set of mapping coefficients to every row; the row processor does not need to identify which sensor-indexed row it is processing to apply correct horizontal mapping coefficients. Similarly, column processing can map entire pseudo-rows into image pixel-indexed rows, e.g. into a final image, by applying a vertical scaling factor to every element or column across a pseudo-row or rows; the column processor does not need to identify a sensor column from which image pixel-indexed information was derived in order to apply correct vertical mapping coefficients across a pseudo-row.

Positioning a sensor array out of alignment with the array of source locations in embodiments of the present invention may break the pattern regularities, e.g. the scaling factor relationships between elements of a sensor data set and a final image plane, that make separable reconstruction possible. When an angular offset exists between a source and sensor, mapping sensor data along sensor rows into an image plane can require applying both column-specific scaling factors as before but also row-specific offsets. Similarly, mapping sensor data into an image plane along sensor columns can entail applying row-specific scaling factors as well as a column-specific offsets. A reconstruction method following that which was previously described may accurately process rows of the sensor data set by providing a row processor for each row of sensor containing mapping coefficients that comprise both scaling factors and offsets. However, applying correct column-specific offsets during column processing would be impossible since no sense of sensor columns exists once data has been mapped into pseudo-rows. Further embodiments of the present invention provide manners in which the benefits of an angularly offset sensor may be incurred without sacrificing the potential to optimize efficiency in image reconstruction.

In one embodiment of the present invention, information sufficient for independent row and column processing may be maintained for separable reconstruction by altering the structure of the sensor data set prior to or during row or column processing. In this embodiment, rows of a sensor data set can be associated with unique y-coordinates of the source, e.g. relative to a y-axis that is aligned with columns of discrete source locations, rather than with the physical rows of elements along a sensor. These "coordinate-indexed" rows may have empty or non-populated columns; each row may contain data in columns only where a sensor element shares the row's unique y-coordinate. Forming data sets of coordinate-indexed rows in this manner can remove the need for applying column-dependent offsets during columns processing, the offsets being essentially incorporated into the structure of the data set, and thereby enable an implementation of separable reconstruction.

Figures 11, 12:
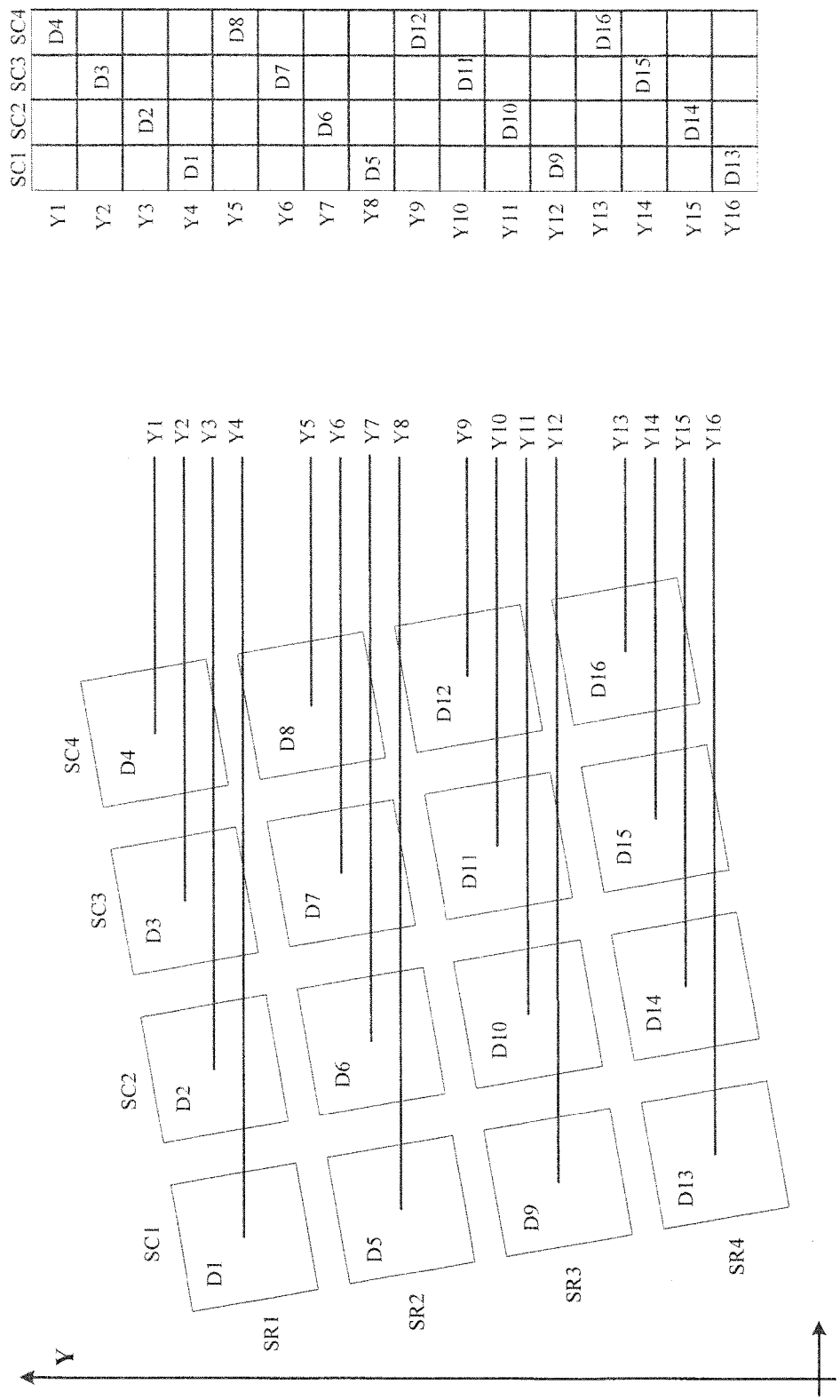
FIG. 11 is a diagram illustrating allocation of sensor data into source coordinate-indexed rows in one embodiment of the present invention.
FIG. 12 is a diagram representing a coordinate-indexed data set of an embodiment of the present invention.

FIG. 11 is a diagram illustrating allocation of sensor data into source coordinate-indexed rows in one embodiment of the present invention. FIG. 11 represents a 4×4 array of sensor elements, where sensor rows are labeled SR1 through SR4 and sensor columns are labeled SC1 through SC4. Elements are labeled D1 through D16. The y-axis shown in FIG. 11 may be referenced to columns of a source array. Since the sensor of this embodiment is offset relative to the source, sensor elements D1 through D16 are positioned at a plurality of unique positions along this axis, labeled here as Y1 through Y16.

In systems where rows and columns of a source and sensor are angularly aligned rows and columns of a sensor data set may correspond to rows and columns of the sensor array; if the sensor of FIG. 11 was not offset relative to a source, it may be convenient to allocate sensor data in a 4×4 matrix where rows were indexed SR1 through SR4 and columns where indexed SC1 through SC4. However, for reasons previously described this type of data set cannot be utilized for separable reconstruction where an angular offset exists. In this embodiment of the present invention, data from the sensor array is allocated in rows according to the unique y-positions of sensor elements, Y1 through Y16. FIG. 12 is a diagram representing a coordinate-indexed data set of an embodiment of the present invention. FIG. 12 shows the placement of each individual sensor datum, the values associated with each element D1 through D16 of FIG. 11, into an appropriate row of a coordinate-indexed data set. For example, the datum associated the first sensor element, D1, is allocated to a row indexed by its unique y-coordinate, Y4. The datum associated with the second sensor element, D2, is allocated to a row indexed by its unique y-coordinate, Y3, and so forth.

The length of coordinate-indexed rows can be constant through a data set. In one embodiment of the present invention, the length of each coordinate-indexed row is equal to the number of columns of sensor elements on the sensor. For example, the data set of FIG. 12 has four columns, corresponding to the four sensor columns SC1 through SC4. It can be seen that coordinate-indexed rows in this embodiment may be sparsely populated; since only one sensor element, D4, is associated with unique y-position Y1, three columns, SC1 through SC3, of this coordinate-indexed row are empty.

In one embodiment of the present invention, separable reconstruction can be implemented using row processors and column processors. Row processors and column processors can be in hardware, firmware, software, or a combination of any of the three. A row processor may exist for every coordinate-indexed row of a given sensor data set and may contain a set of mapping coefficients which can be applied to sensor element data populating a given coordinate-indexed row to map that data to appropriate image pixel-indexed columns of a pseudo-row. In this embodiment, pseudo-rows may also be coordinate-indexed.

Alternatively, a single row processor, or a number of row processors less than the number of coordinate-indexed rows, may be utilized. As memory buffers, e.g. row buffers, may be used to store data corresponding to a given sensor element and data may be handled in row processors one column, e.g. one element or datum, at a time, a row processor may be switched between buffers and thereby handle data from multiple sensor elements. A single row processor, or a number of row processors less than the number of virtual rows, may contain a set or sets of mapping coefficients which can be applied to sensor element data populating various coordinate-indexed rows and may map these row elements into image pixel-indexed columns, e.g. into pseudo-rows. Alternatively, an additional processor can calculate appropriate mapping coefficients, including but not limited to scaling factors and offsets, that should be applied along a given coordinate-indexed row, and transmit these coefficients to a row processor before or as it processes said coordinate-indexed row.

Once row processors have processed the coordinate-indexed rows of FIG. 12, e.g. mapped datum D1 through D16 into appropriate image pixel-indexed columns, sixteen coordinate-indexed pseudo-rows may exist. In the previous description of a separable reconstruction method no information about the unique y-coordinate configurations of each column could be recovered once rows had been processed; the sense of sensor columns had been lost by the time data was formed into pseudo-rows. However, in this embodiment of the present invention, each pseudo-row is associated with a unique y-coordinate, so that the y-coordinate information required for column processing is readily available. A column processor can contain a mapping coefficient that translates the unique y-coordinate associate with a coordinate-indexed pseudo-row into a unique y-coordinate of an image plane, distributing it into an appropriate image pixel-indexed row.

A significantly greater number of coordinate-indexed rows than sensor-indexed rows may be generated for a given data set. For example, if a sensor array has m physical rows of n physical columns, angularly offsetting it can create n unique y-coordinates per sensor-indexed row, e.g. m*n coordinate-indexed rows. A column processor or processors may therefore need to process n times the number of rows for an offset sensor in this embodiment than for a non-offset sensor. Embodiments of the present invention which have been described are in no way limited to 4×4 element sensors but can be applied to sensors of any number of elements. For example, the numbers of rows or columns of sensor elements, e.g. the values of m and n, may be any numbers between 1 and 1,000. Thus, the number of coordinate-indexed rows can become quite large. In a number of following embodiments of the present invention, predetermined approximations can be made for the x- and y-coordinates of sensor elements in order to increase the number of populated elements per coordinate-indexed row and decrease the number of coordinate-indexed rows to be processed.

Figure 13:
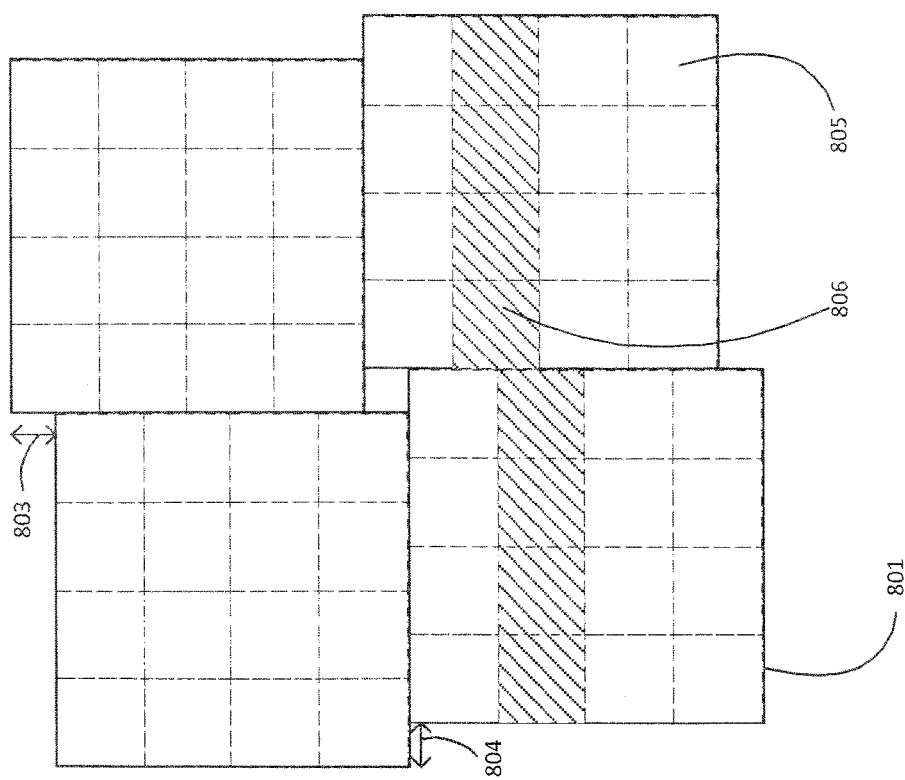
FIG. 13 is a diagram showing a four-segment approximation of an 8×8 element sensor of one embodiment of the present invention.

In one embodiment determination of mapping coefficients for each sensor datum and the allocation of sensor data into coordinate-indexed rows can be based on an approximation of a sensor as a segmented array wherein adjacent segments have been shifted horizontally and vertically relative to one another. The horizontal and vertical shifts between segments can be related to the amount of angular offset between source and sensor. FIG. 13 is a diagram showing a four-segment approximation of an 8×8 element sensor of one embodiment of the present invention. In this approximation, sensor elements are grouped into four segments, which are separated by vertical shift 803 and horizontal shift 804 relative to one another. It can be seen that in each sensor-indexed row, e.g. sensor-indexed row 806, two unique y-coordinates are created; sensor data may be allocated into a total of 16 coordinate-indexed rows rather than the 64 coordinate-indexed rows that may be utilized in a non-approximate implementation.

While the embodiment of FIG. 13 approximates an offset 8×8 element sensor, sensors of any even number of elements may be approximated in the same manner of segmenting and segment-shifting. For example, sensors of 2×2 elements, 4×4 elements, 16×16 elements, 20×20 elements, 30×30 elements, 40×40 elements, 50×50 elements, 60×60 elements, 70×70 elements, 80×80 elements, 90×90 elements, 100×100 elements, 110×100 elements, 120×120 elements, 130×130 elements, 140×140 elements, 150×150 elements, 160×160 elements, 170×170 elements, or any other number of elements between the enumerated values may be modeled as in the embodiment of FIG. 13.

Figure 14:
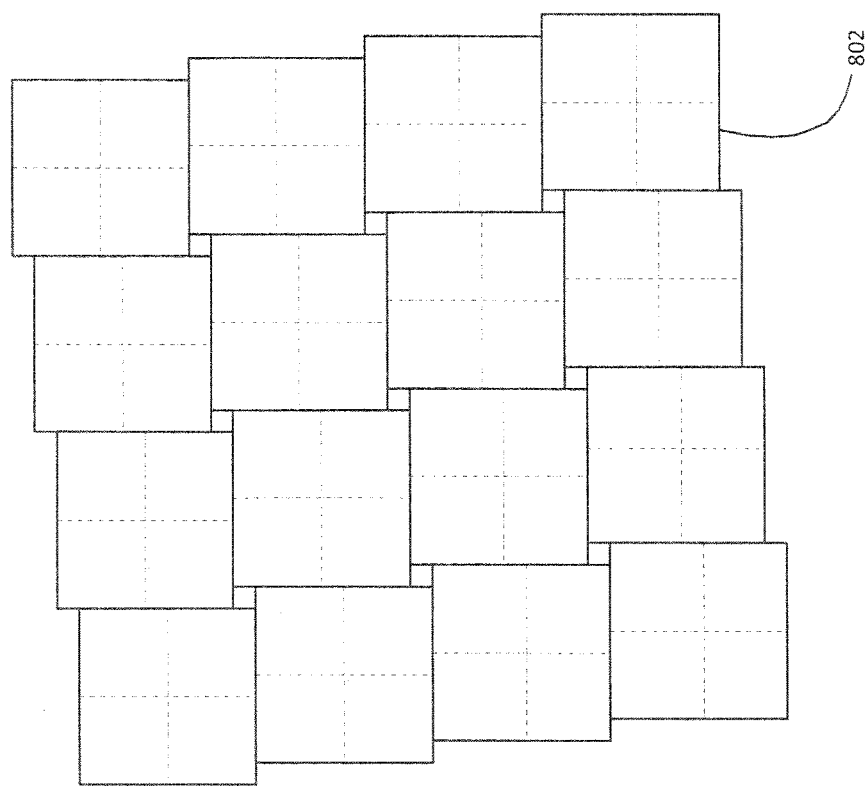
FIG. 14 is a diagram showing a sixteen-segment approximation of an offset 8×8 element sensor of one embodiment of the present invention.

The amount by which sensor segments are shifted in such an approximation may be related to the size of the angular offset between the source and sensor and with the number of segments being utilized for the approximation. More than or fewer than four segments can also be defined for this type of approximation. FIG. 14 is a diagram showing a sixteen-segment approximation of an offset 8×8 element sensor of one embodiment of the present invention. The embodiment of FIG. 14 may approximate a sensor of the same number of elements and with the same angular offset relative to a source as the embodiment of FIG. 13 but may provide for a relatively higher fidelity reconstruction; approximation models with higher numbers of segments may better represent rotated or angularly offset. However, 32 coordinate-indexed rows for processing are created in the embodiment of FIG. 14 compared to the 16 created in the embodiment of FIG. 13. A number of segments chosen for this type of approximation may optimize reconstruction quality given the system resources and time available for processing.

In embodiments of the present invention, angularly offset sensors may be modeled with 4, 9, 16, 25, 36, or 49 segments or any number of segments between 4 and 10,000. The number of segments across a sensor face, e.g. in segment rows, may or may not be equal to the number of segments down a sensor face, e.g. in segment columns. Segments may be square or rectangular. The horizontal and vertical shifts between segments in these approximations, e.g. horizontal shift 804 and vertical shift 803, may be any number or fraction of sensor elements such as ¼ elements, ½ elements, ¾ elements, 1 element, 5/4 elements, 3/2 elements, 7/2 elements, 2 elements, and so forth, and any integer or non-integer number of elements between, above or below the enumerated values.

Figure 15:
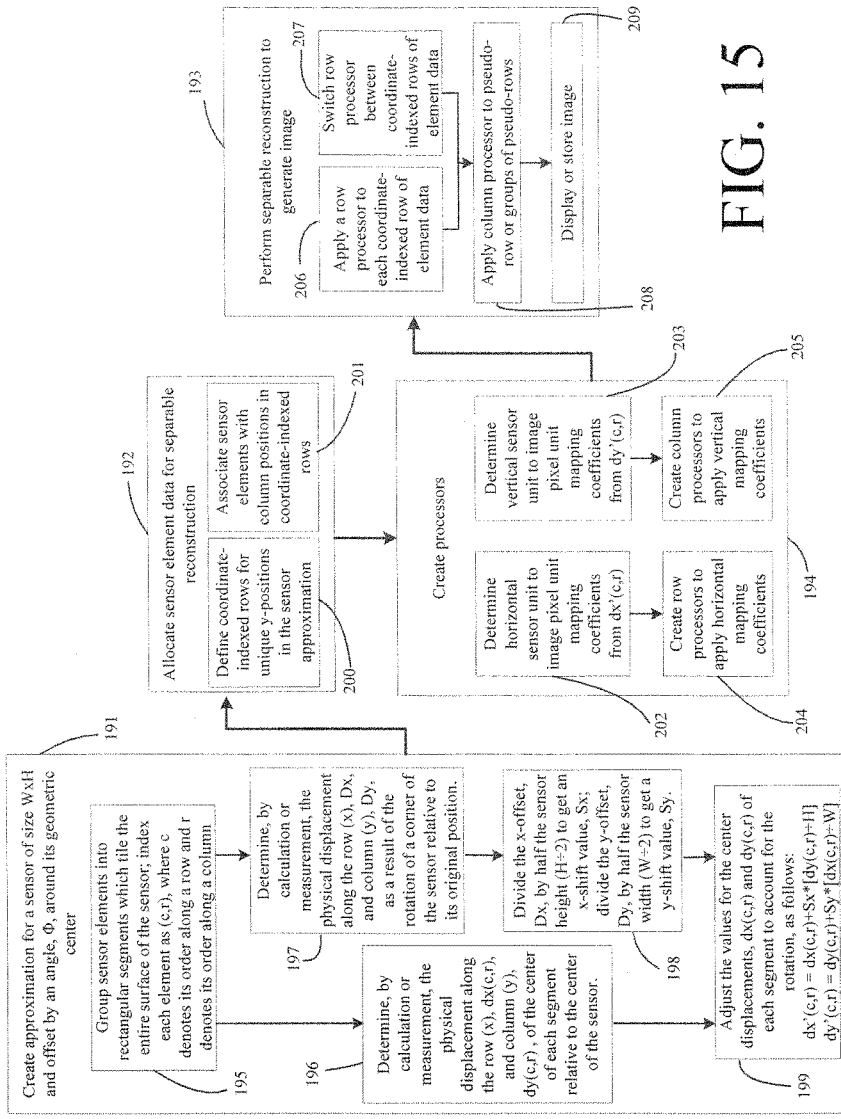
FIG. 15 is a flow diagram illustrating the incorporation of a segment approximation within a separable reconstruction method of one embodiment of the present invention.
Figure 16:
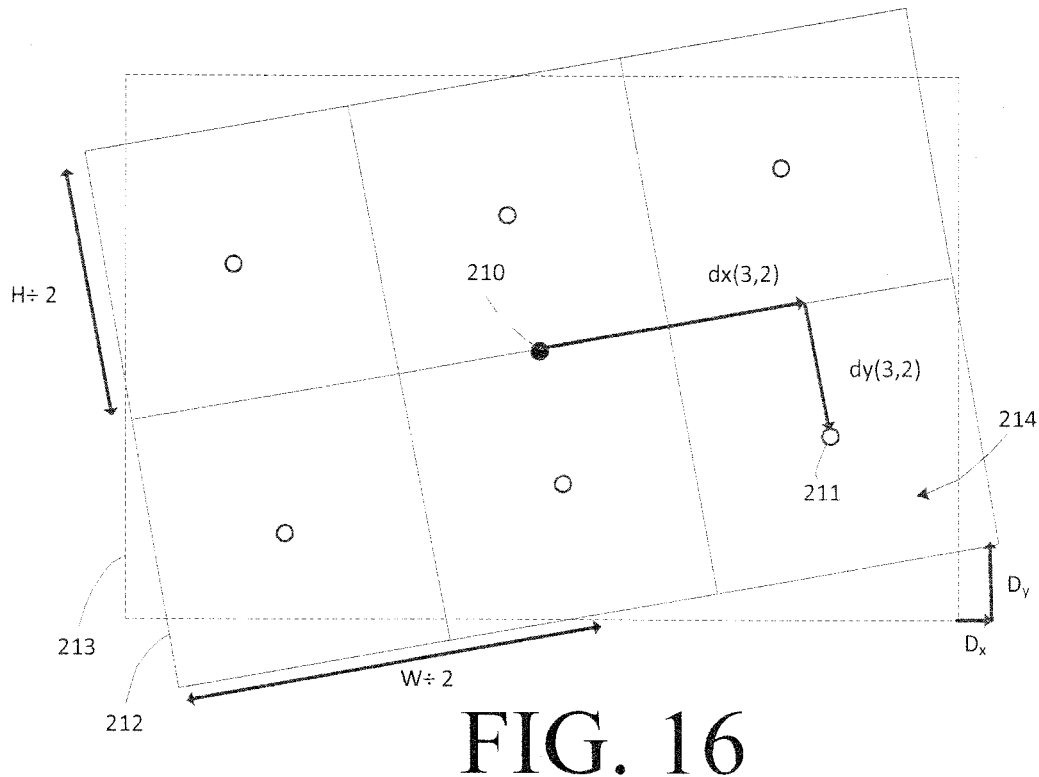
FIG. 16 is a diagram illustrating a rectangular, angularly offset sensor that has been segmented in an approximation method of the present invention.

FIG. 15 is a flow diagram illustrating the incorporation of a segment approximation within a separable reconstruction method of one embodiment of the present invention. In FIG. 15, block 191 contains possible steps for approximation of a sensor of width, W, and height, H, and offset by an angle, ϕ, around its geometric center relative to a source. Step 195 entails the grouping of all sensor elements into rectangular segments. FIG. 16 is a diagram illustrating a rectangular, angularly offset sensor that has been segmented as in step 195. Sensor 212 is angularly offset around its geometric center 210 from its non-offset position 213. In FIG. 16 sensor elements, which are omitted from the illustration for clarity, of sensor 212 can be grouped into six segments, such as segment 214; segment 214 and other segments may comprise any number of elements, for example, a sixth of the elements of the full sensor. Segments may be denoted by a pair of values, (c, r), where c denotes an order along a row, e.g. the second segment across a row may correspond to c=2, and r denotes an order along a column, e.g. the second segment down a column may correspond to r=2. Thus, segment 214 may be denoted segment (3,2).

Step 196 may entail the determination of the distance along the direction of sensor element rows, dx(c, r), and the distance along the direction of sensor element columns, dy(c, r), between the center of each segment relative and the geometric center of the sensor. For example, in FIG. 16 dx(3,2) and dy(3,2) are indicated. Values for each segment of dx(c, r) and dy(c, r) may be determined in any manner, for example by analytical calculation, considering the number of elements in a segment, element spacing, or other factors; physical measurement; or any combination of the two.

Step 197 may entail the determination, by calculation, measurement, or other method, of the physical displacement along the row, $D_x$, and along the column, $D_y$, of a corner of an angularly offset sensor relative to its position when aligned with the source. For example, $D_x$ and $D_y$ are shown in FIG. 16 as the distances between a corner of angularly offset sensor 212 and a corner of aligned position 213. An x-shift value for a segment approximation, $S_x$, can be obtained by dividing $D_x$ by half the sensor height, e.g. H/2, and a y-shift value by dividing $D_y$ by half the sensor width, e.g. W/2, in step 198.

Figure 17:
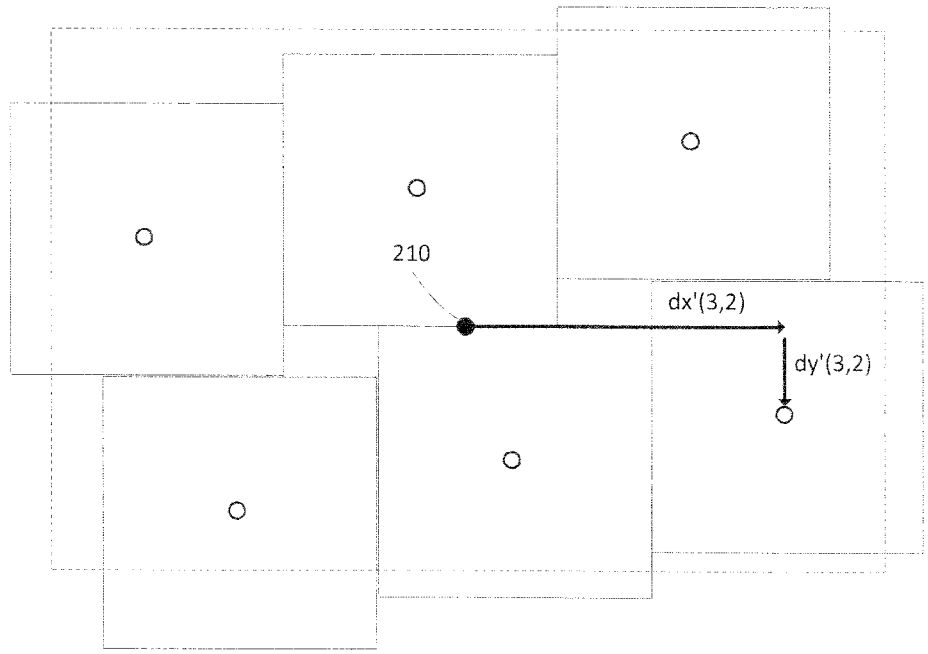
FIG. 17 is a diagram illustrating a segmented model that may be created for an angularly offset sensor in one embodiment of the present invention.

Step 196 may be performed before, concurrently with, or after step 197 and step 198. In step 199 the displacements of segment centers from the sensor center of a segmented model, dx'(c, r) and dy'(c, r), can be calculated as:

$$dx'(c,r)=dx(c,r)+S_x*[dy(c,r)\div H]$$

$$dy'(c,r)=dy(c,r)+S_y*[dx(c,r)\div H]$$

with dx(c, r) and dy(c, r) from step 196 and $S_x$ and $S_y$ from step 198. FIG. 17 is a diagram illustrating a segmented model that may be created for angularly offset sensor 212 by positioning non-rotated segments with center positions given by dx'(c, r) and dy'(c, r).

In the embodiment of FIG. 15, block 192, the allocation of sensor element data for separable reconstruction, and block 194, processor creation, can be completed sequentially or concurrently. In block 192 sensor elements in a segmented model can be assigned to coordinate-indexed rows as previously described, e.g. with respect to the embodiment of FIG. 11 and FIG. 12; step 200 can comprise defining a coordinate-indexed row for each unique y-position created in the sensor approximation of block 191, and step 201 may comprise associating sensor element data with appropriate column positions within said coordinate-indexed rows. In block 194 horizontal mapping coefficients can be determined from dx'(c, r) and vertical mapping coefficients can be determined from dy'(c, r) in step 202 and step 203, respectively. For example, the locations of elements in a segmented model can be determined from the location of their encompassing segment, [dx'(c, r), dy'(c, r)]. Row processors can be created in step 204 and column processors in step 205. In step 204, a number of row processors equal to the number of coordinate-indexed rows defined in step 200 may be created, or a number of row processors less than said number of virtual rows, including one, may be created, as previously described.

An efficient image reconstruction from sensor element data can then be accomplished in block 193. Coordinate-indexed rows can be processed to form pseudo-rows. If a row processor was created for each coordinate-indexed row in step 204, a processor may be applied to each coordinate-indexed row, as in step 206. In step 206, each coordinate-indexed row may be processed simultaneously, if sufficient computing power is available, or sequentially. Alternatively, if a lesser number of row processors was created in step 204, the processor(s) may be applied to multiple coordinate-indexed rows, e.g. switched between locations in row buffers containing element data, as in step 207. It is possible that block 194 and step 206 may be repeated for sensor data corresponding the each discrete source location prior to step 208, column processing. Once a predetermined number of data sets have been mapped into pseudo-rows, or at any other time, column processors created in step 205 may be applied to complete the separable reconstruction. Indicated by step 209, the image may be displayed, stored, or otherwise utilized.

Block 191, block 192, and block 194 may be executed at any time before, during, or after image data acquisition. Steps 202 through 208 may be repeated a number of times corresponding to the number of discrete source locations, e.g. number of sensor data sets, that contribute to a final image. Block 193 and block 194 may also be repeated in order to reconstruct multiple planes, e.g. slices at different distances between the source and sensor. Planes may be displayed independently or overlaid for depth. Blocks and steps in the embodiment of FIG. 15 may be implemented in hardware, software, firmware, or any combination thereof.

The parameters and calculations of block 191 may also be considered in the selection of an optimal amount of angular offset to utilize between a source and sensor. For example, an angular offset may be utilized for which the quantities $D_x$ and $D_y$, and thus $S_x$, $S_y$, dx'(c, r), and dy'(c, r) are rational. Embodiments of the present invention comprising a sensor offset by an integer number of elements per length, e.g. one, two, or three sensor elements per length, may cause the above quantities to be rational; a sensor may be offset such that $D_x$ or $D_y$ equals one, two, three, or another integer or rational number of sensor elements.

Approximations or models other than the segmented approach that has been described can also be utilized to decrease processing time in embodiments of the present invention. Such approximations or models may include but are not limited to rounding, grouping, or otherwise manipulating the unique y-coordinates of sensor elements across a sensor row in embodiments of the present invention in a predetermined fashion to decrease the number of coordinate-indexed rows to be processed.

Increasing the size of a sensor, e.g. increasing the numbers of rows and columns of a sensor array, can increase the field of view of an imaging system. However, increasing the number of sensor elements can also increase the processing demands of the system, particularly in embodiments of the present invention wherein m*n coordinate-indexed rows can be created during reconstruction. A rectangular sensor may be utilized to provide a relatively long field of view in one direction and a reasonable but smaller field of view in the other, which can be useful for a variety of fluoroscopic procedures. The number of coordinate-indexed rows created for reconstruction can be limited by segment approximations as previously described.

Figure 18:
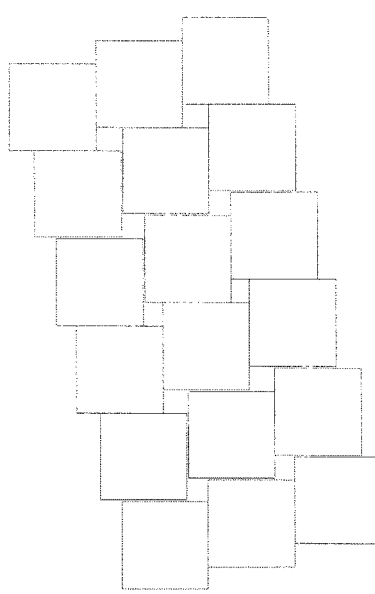
FIG. 18 is a diagram illustrating a segment approximation of a rectangular sensor in one embodiment of the present invention.

FIG. 18 is a diagram illustrating a segment approximation of a rectangular sensor in one embodiment of the present invention. A rectangular sensor may be approximated as having a different number of square segments in its rows than in its columns, as in the embodiment of FIG. 15, but may also be approximated as having an equal number of rectangular segments in its rows and columns or in any other manner.

Figure 19:
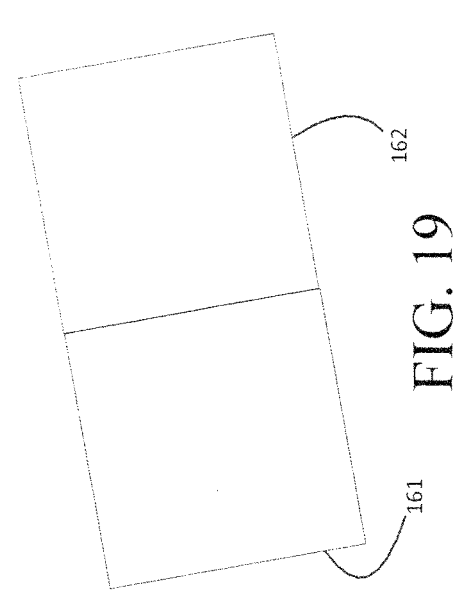
FIG. 19 is a diagram illustrating an embodiment of the present invention wherein two square sensors are positioned to form a rectangular sensor offset relative to a source.

FIG. 19 is a diagram illustrating an embodiment of the present invention wherein two square sensors are positioned to form a rectangular sensor offset relative to a source. Both square sensors, or "tiles," can acquire data during imaging, or a single tile can acquire data. This embodiment may provide a relatively long field of view in the direction along the longer dimension of the rectangular sensor if both tiles are utilized or an equally dimensioned field of view if a single tile is utilized.

Figure 20:
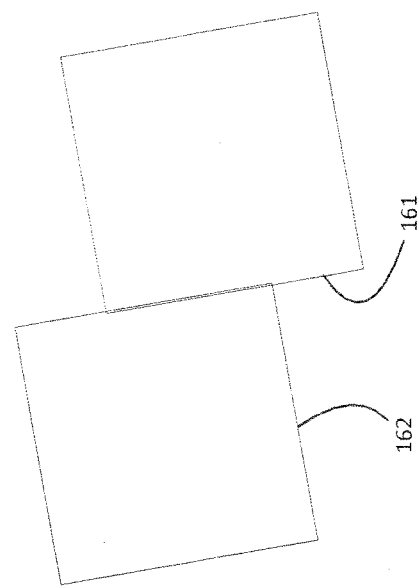
FIG. 20 is a diagram illustrating an embodiment of the present invention also comprising a two-tile sensor.

FIG. 20 is a diagram illustrating an embodiment of the present invention also comprising a two-tile sensor. However, in the embodiment of FIG. 20 first tile 161 is translated horizontally relative to the embodiment of FIG. 19 so that it is positioned at the opposite side of second tile 162. Tile 161 is shown to the right of tile 162 since this horizontal translation description may capture appropriate vertical tile positions for one embodiment of the invention. However, similar embodiments can comprise two rotated detector tiles in a non-rectangular configuration with other horizontal and vertical positions relative to one another. The numbering of tiles 161 and 162 in FIG. 20 may be reversed without significant impact for reconstruction or other aspects.

Both of the embodiments of FIG. 19 and FIG. 20 may incur the benefits of an increased field of view due to the large surface area of the combined sensor arrays as well as the benefits of improved sampling resolution from an angular offset between source and sensor. However, the configuration of sensor elements in the embodiment of FIG. 20 may allow for particularly efficient image reconstruction. As previously described, it may be desirable for a system to be operable in modes where only first tile 161 is utilized or only second tile 162 is utilized, as well as a mode where both first tile 161 and second tile 162 are utilized. A system may be operated utilizing only a single tile during a fluoroscopy-guided procedure requiring a relatively small field of view, or utilizing both tiles during a fluoroscopy-guided procedure requiring a relatively large field of view. In the embodiment of FIG. 19, the number of sensors per full length by which the rectangular, two-tile sensor array is offset is twice the number of sensors per full length by which first tile 161 or second tile 162 is offset. In the embodiment of FIG. 20 the number of sensors per full length by which the full, two-tile sensor array is offset is the same number of sensors per full length by which first tile 161 or second tile 162 is angularly offset. For example, if first tile 161 or second tile 162 were offset by one sensor element per full sensor length, the two-tile sensor in FIG. 19 would be offset by two sensor elements per full length whereas the two-tile sensor in FIG. 20 would be offset by one sensor element per full length. As a result, reconstructing sensor data from the embodiment of FIG. 19 may be handled differently in modes where both tiles are utilized than where a single tile is utilized; a larger number of coordinate-indexed rows may be defined and processed when both tiles are utilized than when a single tile is utilized. In the embodiment of FIG. 20 the same number of and vertical indices for coordinate-indexed rows may be utilized during single- and two-tile reconstructions. In addition to decreasing processing time for the two-tile case relative to the embodiment of FIG. 19, this feature can result in little modification being necessary between reconstruction processes for the one- and two-tile case.

Figure 21:
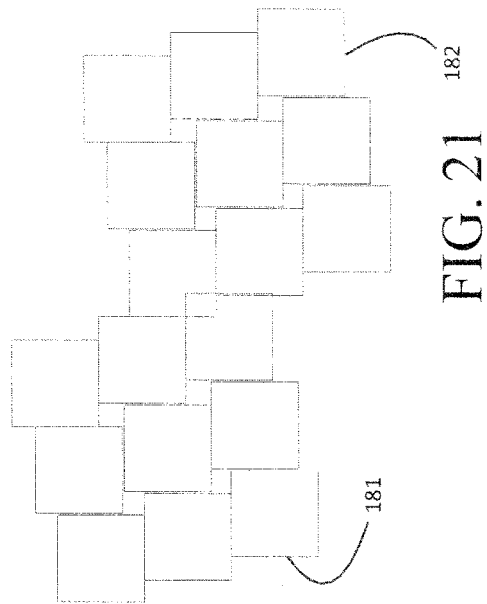
FIG. 21 is a diagram showing a manner of approximating sensor element positions for a two-tile sensor configuration by grouping elements into segments in one embodiment of the present invention.

An implementation of separable reconstruction from the two-tile sensor configuration of the embodiment of FIG. 20 can utilize a segmented approximation or be non-approximate. FIG. 21 is a diagram showing a manner of approximating sensor element positions for a two-tile sensor configuration by grouping elements into segments in one embodiment of the present invention. Separable reconstruction may be implemented according to first segment group 181 if only first tile 161 is utilized, to second segment group 182 if only second tile 162 is utilized, or to both first segment group 181 and second segment group 182 if the full, two-tile sensor is utilized. In FIG. 21, some overlap is shown between first segment group 181 and second segment group 182. However, in practice the amount by which the sensor is offset can be very small, e.g. a single sensor element per full length of the sensor or other small integer numbers of sensor elements per full length of the sensor, for which little to no overlap between segment groups.

In one embodiment of the present invention, the two-tile sensor of FIG. 20 can be incorporate in a cardiac fluoroscopy system. The system may utilize the two-tile sensor to produce high resolution x-ray video for full cardiac fluoroscopy, but may utilize only a single tile, e.g. first tile 161 or second tile 162, to produce high resolution x-ray video for cardiac electrophysiology. The sampling resolution benefits created by an angular offset between source and sensor may be present for both applications. The two-tile sensor mode can provide an extended field of view, and the single-tile sensor mode can expose the patient to relatively less x-ray radiation.

Embodiments of the present invention may comprise tomosynthetic imaging systems utilizing rotated or angularly offset, multi-element sensors of any shape or size. Sensors may, but need not, comprise multiple smaller sensor arrays or tiles is in the embodiments of FIG. 19 and FIG. 20.

Embodiments of the present invention comprising real-time row-processing and aggregated column processing may be particularly efficient for an illumination pattern that runs across rows of discrete source locations. However, the direction of the scan may be reversed; source locations along a column may illuminate the image space sequentially, e.g. top to bottom, before restarting at the beginning of the next column. In this case, it may be more efficient to process column data first, e.g. during the scan, implementing coordinate-indexed columns and column processors, and handle row processing after a predetermined number of data sets have been column-processed. While specific embodiments of the present invention may refer to a particular order of row and column processing, the order may be reversed without requiring significant changes to the method described. Furthermore, the definitions of rows and columns need not be strictly associated with horizontal or vertical directions. For example, rows and columns may be related to the pattern in which source locations illuminate the image space, the order in which data is received from the sensor, or a variety of other system parameters.

Reconstruction techniques described above are representative only and do not cover all alternatives techniques or details within. Additional reconstruction aspects, described for a non-offset sensor but which may be utilized, can be found in U.S. Pat. No. 6,178,223 issued Jan. 23, 2001, entitled "Image Reconstruction Method and Apparatus," U.S. Pat. No. 5,644,612 issued Jul. 1, 1997 entitled "Image Reconstruction Methods," U.S. Pat. No. 5,751,785 issued May 12, 1998 entitled "Image Reconstruction Methods," U.S. Pat. No. 6,181,764 issued Jan. 30, 2001 entitled "Image Reconstruction for Wide Depth of Field Images," all of which are herein incorporated by reference.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An X-ray imaging system comprising:
   a radiation source configured to emit radiation from a plurality of discrete emissive locations through an imaging volume, wherein said discrete emissive locations of said radiation source are arrayed in rows and columns;
   a radiation sensor comprising a plurality of sensing elements, wherein said plurality of sensing elements comprises a plurality of segments of sensing elements, wherein each of said segments is angularly offset around its geometric center so that an angular offset exists between said sensing elements and said rows and said columns of said discrete emissive locations; and a processor configured to process and allocate responses of said sensing elements to said radiation from a discrete emissive location of said discrete emissive locations into a respective memory location.

2. The X-ray imaging system of claim 1 wherein said angular offset is less than 90 degrees.

3. The X-ray imaging system of claim 1 wherein said angular offset is less than 5 degrees.

4. The X-ray imaging system of claim 1 wherein said segments comprise: a first segment comprising columns of sensing elements and at least one row of sensing elements, and a second segment adjacent to said first segment comprising columns of sensing elements and at least one row of sensing elements.

5. The X-ray imaging system of claim 4 wherein said columns of said first segment are parallel with said columns of said second segment and wherein a row of said first segment is offset from a row of said second segment along a direction of said columns of sensing elements.

6. A method comprising:
positioning an object for imaging between a radiation source having rows and columns of discrete emissive locations and a radiation sensor having rows and columns of sensing elements, wherein said plurality of sensing elements comprises a plurality of sensing elements, each of said segments comprising a plurality of said columns and at least one of said rows, wherein each of said segments is angularly offset around its geometric center so that an angular offset exists between said rows and said columns of said sensing elements and said rows and said columns of said discrete emissive locations, respectively;
illuminating a portion of said object with radiation from one of said discrete emissive locations; and
detecting responses of said sensing elements to said radiation.

7. The method of claim 6 further comprising:
allocating said responses into a data set wherein data rows correspond to unique positions along a direction of columns of said discrete emissive locations; and
determining mapping coefficients relating said data set to an image plane.

8. The method of claim 7 further comprising:
mapping said data set into image plane rows along a first dimension.

9. The method of claim 8 further comprising:
illuminating additional portions of said object sequentially by additional discrete emissive locations;
detecting additional responses from said sensing elements;
allocating said additional responses from said sensing elements into additional data sets;
mapping said additional data sets into said image plane rows along said first dimension;
aggregating a predetermined number of said image plane rows; and
mapping said image plane rows into image plane columns along a second dimension.

10. The method of claim 6 wherein said angular offset is less than 90 degrees.

11. The method of claim 6 wherein said angular offset is less than 5 degrees.

12. The method of claim 6 wherein said segments comprise: a first segment comprising columns of sensing elements and at least one row of sensing elements, and a second segment adjacent to said first segment comprising columns of sensing elements and at least one row of sensing elements, wherein said columns of said first segment are parallel with said columns of said second segment and wherein a row of said first segment is offset from a row of said second segment along a direction of said columns of sensing elements.

13. A method comprising:
positioning a radiation source that has rows and columns of discrete emissive locations;
positioning a radiation sensor that has rows and columns of sensing elements so that radiation from said radiation source is incident on said radiation sensor, wherein said sensing elements comprises a plurality of segments of sensing elements, wherein each of said segments is angularly offset around its geometric center such that an angular offset less than 90 degrees exists between said rows and said columns of said discrete emissive locations and said rows and said columns of said sensing elements;
illuminating a portion of an imaging volume with radiation from one of said discrete emissive locations; and
recording responses of each of said sensing elements.

14. The method of claim 13 wherein said angular offset is less than 5 degrees.

15. The method of claim 13 further comprising:
sequentially illuminating additional portions of said imaging volume by said discrete emissive locations;
recording additional responses of each of said sensing elements; and
reconstructing an image plane from said responses and said additional responses.

16. The method of claim 15 further comprising:
mapping said responses and said additional responses into said image plane in a first dimension as said responses and said additional responses are received.

17. The method of claim 16 further comprising:
aggregating said responses and said additional responses mapped in said first dimension into subsets; and
mapping said subsets into said image plane in a second dimension.

18. The method of claim 15 further comprising:
mapping said responses and said additional responses into said image plane as said responses and said additional responses are received.

19. The method of claim 13 wherein said segments comprise: a first segment comprising columns of sensing elements and at least one row of sensing elements, and a second segment adjacent to said first segment comprising columns of sensing elements and at least one row of sensing elements, wherein said columns of said first segment are parallel with said columns of said second segment and wherein a row of said first segment is offset from a row of said second segment along a direction of said columns of sensing elements.

* * * * *